(12) United States Patent
Holtcamp (10) Patent No.: US 6,495,484 B1
(45) Date of Patent: Dec. 17, 2002

(54) CATALYST SYSTEM AND ITS USE IN A POLYMERIZATION PROCESS

(75) Inventor: Matthew W. Holtcamp, Huffman, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 09/649,746

(22) Filed: Aug. 28, 2000

(51) Int. Cl.[7] ................................................. B01J 31/00
(52) U.S. Cl. ........................ 502/152; 502/156; 502/132; 502/87; 526/160; 526/172; 526/114; 526/119; 526/348; 526/943
(58) Field of Search ................... 502/156, 152, 502/132, 87; 526/160, 172, 114, 119, 348, 943

(56) References Cited

U.S. PATENT DOCUMENTS

| | | | |
|---|---|---|---|
| 5,602,269 A | 2/1997 | Biagini et al. | 556/170 |
| 5,712,365 A * | 1/1998 | Arai et al. | 528/498 |
| 5,753,577 A * | 5/1998 | Hamura et al. | 502/113 |
| 5,763,549 A | 6/1998 | Elder et al. | 526/153 |
| 5,895,771 A | 4/1999 | Epstein | 502/103 |
| 6,121,396 A * | 9/2000 | Sone et al. | 526/153 |

FOREIGN PATENT DOCUMENTS

| | | |
|---|---|---|
| WO | WO99/06414 | 2/1999 |
| WO | WO99/15534 | 4/1999 |

OTHER PUBLICATIONS

Harney et al., Aust. J. Chem., 27, 1639–53 (1974).*
Harney, D.W. et al., Aust. J. Chem.(1974) 27, 1639–53, "C–Methylation of Alcohols by Trimethylaluminum".

* cited by examiner

Primary Examiner—David W. Wu
Assistant Examiner—Ling-Siu Choi
(74) Attorney, Agent, or Firm—Lisa Kimes Jones (57) ABSTRACT

Disclosed are polymerization catalyst activator compositions which include a carbonium cation and an aluminum containing anion. These activator compositions are prepared by combining a carbonium or trityl source and with an aluminum containing complex, preferably a perfluorophenylaluminum compound. Also disclosed are polymerization catalyst systems including the activator composition of the invention, and processes for polymerizing olefins utilizing same.

17 Claims, 2 Drawing Sheets

CATALYST SYSTEM AND ITS USE IN A POLYMERIZATION PROCESS

FIELD OF THE INVENTION

The present invention relates to catalyst activator compositions, to methods of making these activator compositions, to polymerization catalyst systems containing these activator compositions, and to olefin(s) polymerization processes utilizing same. More specifically, the present application relates to the preparation and use of carbonium salt complexes containing at least one anionic aluminum, to catalyst systems containing these complexes, and to polymerization processes utilizing same.

BACKGROUND OF THE INVENTION

Polymerization catalyst compounds, including bulky ligand metallocene catalyst compounds, are typically combined with an activator (or co-catalyst) to yield compositions having a vacant coordination site that will coordinate, insert, and polymerize olefins. Known activators included alumoxane, modified alumoxanes, aluminum alkyls, and ionizing activators. Examples of neutral ionizing activators include Group 13 based Lewis acids having three fluorinated aryl substituents, and examples of ionic ionizing activators include ammonium cations or trityl cations (triphenylcarbenium) combined with noncoordinating/ weakly coordinating borate or aluminate anions.

Alumoxane activators are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. A variety of methods for preparing alumoxanes and modified alumoxanes are described in U.S. Pat. Nos. 4,665, 208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publication WO 94/10180. Known alumoxane activators are also disclosed in U.S. Pat. No. 5,041,584. Another known activator, modified methyl alumoxane in heptane (MMAO3A) is commercially available from Akzo Chemicals, Inc., Houston, Tex. Alumoxanes, however, must generally be present in a large excess over the catalyst compound to be effective activators, which significantly increases the costs of such catalyst systems.

Aluminum alkyl compounds, including trialkylaluminums and alkyl aluminum chlorides, are also known to be useful as activators. Examples of these compounds include trimethylaluminum, triethylaluminum, triisobutylaluminum, tri-n-hexylaluminum, tri-n-octylaluminum and the like.

Neutral ionizing activators include Group 13 based Lewis acids, having three fluorinated aryl substituents, are capable of activating olefin polymerization catalysts. Specific examples of these activators include trisperfluorophenyl boron and trisperfluoronapthyl boron. Trisperfluorophenylborane, is demonstrated in EP-A1-0 425 697 A1 and EP-B1-0 520 732 to be capable of abstracting a ligand for cyclopentadienyl derivatives of transition metals while providing a stabilizing, compatible noncoordinating anion. See also, Marks, et al, J. Am. Chem. Soc. 1991, 113, 3623–3625. The noncoordinating anions are described to function as electronic stabilizing cocatalysts, or counterions, for cationic metallocene complexes which are active for olefin polymerization. The term noncoordinating anion as used herein applies to noncoordinating anions and coordinating anions that are at most weakly coordinated to the cationic complex so as to be labile to replacement by olefinically or acetylenically unsaturated monomers at the insertion site. The synthesis of Group 13-based compounds derived from trisperfluorophenylborane are described in EP 0 694 548 A1. These Group 13-based compounds are said to be represented by the formula $M(C_6F_5)_3$ and are prepared by reacting the trisperfluorophenylborane with dialkyl or trialkyl Group 13-based compounds at a molar ratio of about 1:1 so as to avoid mixed products, those including the type represented by the formula $M(C_6F_5)_nR_{3-n}$, where n=1 or 2. Utility for the tris-aryl aluminum compounds in Ziegler-Natta olefin polymerization is suggested.

Ionizing ionic activators, for example, include ammonium cations, such as N,N-dimethylanilinium, or trityl cations (triphenylcarbenium or trityl$^+$) combined with noncoordinating/weakly coordinating borate or aluminate anions, such as, for example tetra(perfluorophenyl)borate. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299, 5,447,895 and 5,502,124 and U.S. patent application Ser. No. 08/285,380, filed Aug. 3, 1994, all of which are fully incorporated herein by reference.

Perfluorophenyl-aluminum complexes, however, have been implicated as possible deactivation sources in olefin polymerizations which utilize Trityl$^+$ $B(C_6F_5)_4^-$/ alkylaluminum combinations to activate the catalysts. See, Bochmann, M.; Sarsfield, M. J.; Organometallics 1998, 17, 5908. Perfluorophenylaluminum (toluene), for example, has been characterized via X-ray crystallography. See, Hair, G. S., Cowley, A. H., Jones, R. A., McBurnett, B. G.; Voigt, A., J. Am. Chem. Soc., 1999, 121, 4922. Arene coordination to the aluminum complex demonstrates the Lewis acidity of the aluminum center. Bochmann and Sarsfield have shown that $Cp_2ZrMe_2$ reacts with $Al(C_6F_5)_3$0.5(toluene) with transfer of the $C_6F_5^-$ moiety forming metallocene pentafluorophenyl complexes. These complexes, however, were reported having very low activity compared to the corresponding metallocene dimethyl complexes when activated with $B(C_6F_5)_3$ or Trityl$^+$ $B(C_6F_5)_4^-$.

The supporting of ionic activators, however, typically results in a significant loss of activity. Supported noncoordinating anions derived from trisperfluorophenyl boron are described in U.S. Pat. No. 5,427,991. Trisperfluorophenyl boron is shown to be capable of reacting with coupling groups bound to silica through hydroxyl groups to form support bound anionic activators capable of activating transition metal catalyst compounds by protonation. U.S. Pat. Nos. 5,643,847 and 5,972,823 discuss the reaction of Group 13 Lewis acid compounds with metal oxides such as silica and illustrate the reaction of trisperfluorophenyl boron with silanol groups (the hydroxyl groups of silicon) resulting in bound anions capable of protonating transition metal organometallic catalyst compounds to form catalytically active cations counter-balanced by the bound anions.

Immobilized Group IIIA Lewis acid catalysts suitable for carbocationic polymerizations are described in U.S. Pat. No. 5,288,677. These Group IIIA Lewis acids are said to have the general formula $R_nMX_{3-n}$ where M is a Group IIIA metal, R is a monovalent hydrocarbon radical consisting of $C_1$ to $C_{12}$ alkyl, aryl, alkylaryl, arylalkyl and cycloalkyl radicals, n=0 to 3, and X is halogen. Listed Lewis acids include aluminum trichloride, trialkyl aluminums, and alkylaluminum halides. Immobilization is accomplished by reacting these Lewis acids with hydroxyl, halide, amine, alkoxy, secondary alkyl amine, and other groups, where the groups are structurally incorporated in a polymeric chain. James C. W. Chien, Jour. Poly. Sci.: Pt A: Poly. Chem, Vol. 29, 1603–1607 (1991), describes the olefin polymerization utility of methylalumoxane (MAO) reacted with $SiO_2$ and zirconocenes and describes a covalent bonding of the aluminum atom to the silica through an oxygen atom in the surface hydroxyl groups of the silica.

Additional compounds useful as activators also include those described in PCT publications WO 98/07515, which discloses tris (2,2',2"-nonafluorobiphenyl) fluoroaluminate, WO 98/09996, which describes activating bulky ligand metallocene catalyst compounds with perchlorates, periodates and iodates including their hydrates, WO 98/30602 and WO 98/30603, which describe the use of lithium (2,2'-bisphenyl-ditrimethylsilicate).4THF as an activator for a bulky ligand metallocene catalyst compound, WO 99/18135 which describes the use of organo-boron-aluminum activators, and in EP-B1-0 781 299 which describes using a silylium salt in combination with a non-coordinating compatible anion, all of which are herein fully incorporated by reference. Further activators or methods for activating a bulky ligand metallocene catalyst compound are described in for example, U.S. Pat. Nos. 5,849,852, 5,859,653 and 5,869,723 and WO 98/32775, WO 99/42467 (dioctadecylmethylammonium-bis(tris(pentafluorophenyl)borane)benzimidazolide), which are also fully incorporated herein by reference.

U.S. Pat. No. 5,895,771 discloses a catalyst composition comprising a neutral metallocene and an anionic aluminum containing complex which is a fluorinated alkoxy and/or arylalkoxy aluminate where the fluorinated alkoxy aluminate can be of the formula $A^+(Al(OR)_4)^-$.

Harney, D. W et al., Aust. J. Chem. (1974) 27, 1639, discuss the reaction of triphenylmethanol and trimethylaluminum. Water is reported to catalyze the formation of 1,1,1-triphenylethane from the reaction of trimethylaluminum and $[Me_2AlOC(C_6H_5)_3]_2$.

WO 99/15534 reports the reaction of methylalumoxane and tris-pentafluorophenylaluminum.

WO 99/06414 reports compounds of the formula $[R2B—X—AlR,R]_x$.

While these catalyst activator compounds have been described in the art, there is still a need for improved catalyst activators, for activators suitably for anchoring on supports, and for catalyst systems utilizing such activators.

SUMMARY OF THE INVENTION

This invention provides new polymerization catalyst activator compositions including a carbonium cation and an aluminum containing anion. These activator compositions are prepared by combining a carbonium or trityl source and with an aluminum containing complex, preferably a perfluorophenylaluminum compound. The invention also provides for methods of making the activator compositions of the invention, a polymerization catalyst system which includes the activator composition of the invention, and a process for polymerizing olefins utilizing same.

DETAILED DESCRIPTION OF THE INVENTION

New carbonium salt activator compositions, having an anion containing at least one aluminum atom have been discovered. Preferably, the activator composition of the invention includes a carbonium salt containing an aluminum anion such that in the resulting complex contains at least one anionic aluminum. The activator composition of the invention may be prepared by combining a carbonium or trityl source and with an aluminum containing complex. The resulting trityl-alumoxane complexes have been found to activate polymerization catalyst compounds.

The activators of the invention are the compositions produced by the combination of perfluorophenylaluminum compounds with a trityl source. In one embodiment, the perfluorophenylaluminum compound may be represented by formula (I):

$$Al(C_6F_5)_mR_n \qquad (I)$$

where m+n=3 and each R is independently a monoanionic ligand, hydrogen, an hydroxyl group, an alkyl group, or R may be represented by the formula ArHal, where ArHal a halogenated $C_6$ aromatic or higher carbon number polycyclic aromatic hydrocarbon or aromatic ring assembly in which two or more rings (or fused ring systems) are joined directly to one another or together. Alternatively, R may be represented by formula $[M^{k+}Q_n]^{d-}$ wherein k is an integer from 1 to 3; n is an integer from 2 to 6; n–k=d; M is an element selected from Group 13 of the Periodic Table of the Elements and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms.

An alkyl group may be a linear or branched alkyl radical, alkenyl radical, alkynyl radical, cycloalkyl radical or aryl radicals, an acyl radical, aroyl radical, alkoxy radical, aryloxy radical, alkylthio radical, dialkylamino radical, alkoxycarbonyl radical, aryloxycarbonyl radical, carbomoyl radicals, alkyl- or dialkyl- carbamoyl radical, acyloxy radicals, acylamino radical, aroylamino radical, straight, branched or cyclic alkylene radical, or combination thereof. An arylalkyl group is defined to be a substituted aryl group.

Suitable non-limiting examples of R ligands include: substituted or unsubstituted $C_1$ to $C_{30}$ hydrocarbyl aliphatic or aromatic groups, substituted meaning that at least one hydrogen on a carbon atom is replaced with a hydrocarbyl, halide, halocarbyl, hydrocarbyl or halocarbyl substituted organometalloid, dialkylamido, alkoxy, siloxy, aryloxy, alkysulfido, arylsulfido, alkylphosphido, alkylphosphido or other anionic substituent; fluoride; bulky alkoxides, where bulky refers to $C_4$ and higher number hydrocarbyl groups, e.g., up to about $C_{20}$, such as tert-butoxide and 2,6-dimethylphenoxide, and 2,6-di(tert-butyl)phenoxide; —SR; —$NR_2$, and —$PR_2$, where each R is independently a substituted or unsubstituted hydrocarbyl as defined above; and, $C_1$ to $C_{30}$ hydrocarbyl substituted organometalloid, such as trimethylsilyl.

Examples of ArHal include the phenyl, napthyl and anthracenyl radicals of U.S. Pat. No. 5,198,401 and the biphenyl radicals of WO 97/29845 when halogenated, both incorporated herein by reference. The use of the terms halogenated or halogenation, for purposes of this patent specification and appended claims, mean that at least one third of hydrogen atoms on carbon atoms of the aryl-substituted aromatic ligands are replaced by halogen atoms. More preferably, the aromatic ligands are perhalogenated, where the preferred halogen is fluorine.

In one embodiment, the trityl source is represented by the formula II:

$$(C_6H_5)_3COL \qquad (II)$$

where L is a metal moiety, a metalloid moiety, or L is the same as R as defined above.

A metal moiety is a metal atom containing group. Examples of metal atom(s) are those selected from Groups 3 through 15 and the lanthanide or actinide series of the Periodic Table of Elements. Preferred metals containing groups include Al, K, Mg, Na, Si, Ti and Zr. Non-limiting examples of metal atom containing groups include $AlR_2$, $TiR_3$, $Ti(Bz)_3$ or $ZrR_3$ where R is as defined above and where Bz is benzyl.

A metalloid moiety is an metalloid atom containing group. Examples of metalloid atoms include B, Al, Si, Ge, As, Sb, Te, Po and At.

In one embodiment, L may be represented by formula $[M^{k+}Q_n]^{d-}$ wherein k is an integer from 1 to 3; n is an integer from 2 to 6; n−k=d; M is an element selected from Group 13 of the Periodic Table of the Elements and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, Q having up to 20 carbon atoms.

In one embodiment, the complex resulting from combining the perfluorophenyl aluminum compound of formula I and the trityl source of formula II may be represented generally by formula III:

$$[Al(C_6F_5)_mR_n]_x[(C_6H_5)_3COL]_y \qquad (III)$$

where, in formula II, x and y may or may not be integers and represent the ratio in which the perfluorophenylaluminum complex (formula I) and the trityl source (formula II) were combined, and where R, L, m and n are as defined above.

In another embodiment, the perfluorophenylaluminum complex may be represented generally by formula IV:

$$(AlO)_x(Al)_y(C_6F_5)_z(R)_d \qquad (IV)$$

where, in formula IV, x cannot be 0; x+y≧2; if y=0 then x≧2; R may be OH, R or OR, where R is as defined above; R may bridge to the Al; z+d is ≦1+3(x+y) where x, y, z and d represent the ratio in which the components combine and may or may not be integers.

While not being limited by theory, it is believed that the perfluorophenylaluminum complexes, represented by formulae I and IV, react with the compounds of formula II inserting into the C—O bond and forming an aluminum oxygen bond with the reaction driven by the oxophilicity of the perfluorophenylaluminum complex. In the absence of an anionic moiety available for reaction with the resulting $(C_6H_5)_3C^+$ cation, trityl salts are obtained.

In another embodiment, other activators or methods of activation are contemplated for use with the activator(s) described above. For example, the activators of the invention may be used in combination with other activators including alumoxane, modified alumoxane, tri(n-butyl) ammonium tetrakis (pentafluorophenyl) boron, a trisperfluorophenyl boron metalloid precursor or a trisperfluoronapthyl boron metalloid precursor, polyhalogenated heteroborane anions, trimethylaluminum, triethylaluminum, triisobutylaluminum, tri-n-hexylaluminum, tri-n-octylaluminum, tris(2,2',2"-nona-fluorobiphenyl) fluoroaluminate, perchlorates, periodates, iodates and hydrates, (2,2'-bisphenyl-ditrimethylsilicate).4THF and organo-boron-aluminum compound, silylium salts and dioctadecylmethylammonium-bis(tris(pentafluorophenyl) borane)benzimidazolide or combinations thereof.

Catalyst Compounds

The activator compositions of the invention may be utilized in conjunction with any suitable polymerization catalyst compound or compounds to polymerize olefins. In a preferred embodiment, the catalyst compositions contain alkyl leaving groups. Examples of suitable catalyst compounds include bulky ligand metallocene catalyst compositions, metal containing Group 15 polymerization catalyst compositions and phenoxide transition metal catalyst compositions.

Bulky Ligand Metallocene Catalyst Compositions

The activator compositions of the present invention may be used to activate bulky ligand metallocene catalyst compositions. Generally, these catalyst compounds include half and full sandwich compounds having one or more bulky ligands bonded to at least one metal atom. Typical bulky ligand metallocene compounds are described as containing one or more bulky ligand(s) and one or more leaving group(s) bonded to at least one metal atom.

The bulky ligands are generally represented by one or more open, acyclic, or fused ring(s) or ring system(s) or a combination thereof The ring(s) or ring system(s) of these bulky ligands are typically composed of atoms selected from Groups 13 to 16 atoms of the Periodic Table of Elements. Preferably the atoms are selected from the group consisting of carbon, nitrogen, oxygen, silicon, sulfur, phosphorous, germanium, boron and aluminum or a combination thereof Most preferably the ring(s) or ring system(s) are composed of carbon atoms such as but not limited to those cyclopentadienyl ligands or cyclopentadienyl-type ligand structures or other similar functioning ligand structure such as a pentadiene, a cyclooctatetraendiyl or an imide ligand. The metal atom is preferably selected from Groups 3 through 15 and the lanthanide or actinide series of the Periodic Table of Elements. Preferably the metal is a transition metal from Groups 4 through 12, more preferably Groups 4, 5 and 6, and most preferably the transition metal is from Group 4.

In one embodiment, the bulky ligand metallocene catalyst compounds, which may be utilized with the activator composition of the invention, may be represented by the formula:

$$L^AL^BMQ_n \qquad (V)$$

where M is a metal atom from the Periodic Table of the Elements and may be a Group 3 to 12 metal or from the lanthanide or actinide series of the Periodic Table of Elements, preferably M is a Group 4, 5 or 6 transition metal, more preferably M is zirconium, hafnium or titanium. The bulky ligands, $L^A$ and $L^B$, are open, acyclic or fused ring(s) or ring system(s) and are any ancillary ligand system, including unsubstituted or substituted, cyclopentadienyl ligands or cyclopentadienyl-type ligands, heteroatom substituted and/or heteroatom containing cyclopentadienyl-type ligands. Non-limiting examples of bulky ligands include cyclopentadienyl ligands, cyclopentaphenanthreneyl ligands, indenyl ligands, benzindenyl ligands, fluorenyl ligands, octahydrofluorenyl ligands, cyclooctatetraendiyl ligands, cyclopentacyclododecene ligands, azenyl ligands, azulene ligands, pentalene ligands, phosphoyl ligands, phosphinimine (WO 99/40125), pyrrolyl ligands, pyrozolyl ligands, carbazolyl ligands, borabenzene ligands and the like, including hydrogenated versions thereof, for example tetrahydroindenyl ligands. In one embodiment, $L^A$ and $L^B$ may be any other ligand structure capable of η-bonding to M, preferably $η^3$-bonding to M and most preferably $η^5$-bonding. In yet another embodiment, the atomic molecular weight (MW) of $L^A$ or $L^B$ exceeds 60 a.m.u., preferably greater than 65 a.m.u. In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a hetero-cyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazomacrocycles. Independently, each $L^A$ and $L^B$ may be the same or different type of bulky ligand that is bonded to M. In one embodiment of formula (V) only one of either $L^A$ or $L^B$ is present.

Independently, each $L^A$ and $L^B$ may be unsubstituted or substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl- carbamoyl radicals, acyloxy radicals, acylamino radicals, aroylamino radicals, straight, branched or cyclic, alkylene radicals, or combination thereof. In a preferred embodiment, substituent groups R have up to 50 non-hydrogen atoms, preferably from 1 to 30 carbon, that can also be substituted with halogens or heteroatoms or the like. Non-limiting examples of alkyl substituents R include methyl, ethyl, propyl, butyl, pentyl, hexyl, cyclopentyl, cyclohexyl, benzyl or phenyl groups and the like, including all their isomers, for example tertiary butyl, isopropyl, and the like. Other hydrocarbyl radicals include fluoromethyl, fluroethyl, difluroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methyl-bis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorous, oxygen, tin, sulfur, germanium and the like, including olefins such as but not limited to olefinically unsaturated substituents including vinyl-terminated ligands, for example but-3-enyl, prop-2-enyl, hex-5-enyl and the like. Also, at least two R groups, preferably two adjacent R groups, are joined to form a ring structure having from 3 to 30 atoms selected from carbon, nitrogen, oxygen, phosphorous, silicon, germanium, aluminum, boron or a combination thereof. Also, a substituent group R group such as 1-butanyl may form a carbon sigma bond to the metal M.

Other ligands may be bonded to the metal M, such as at least one leaving group Q. For the purposes of this patent specification and appended claims the term "leaving group" is any ligand that can be abstracted from a bulky ligand metallocene catalyst compound to form a bulky ligand metallocene catalyst cation capable of polymerizing one or more olefin(s). In one embodiment, Q is a monoanionic labile ligand having a sigma-bond to M. Depending on the oxidation state of the metal, the value for n is 0, 1 or 2 such that formula (I) above represents a neutral bulky ligand metallocene catalyst compound.

Non-limiting examples of Q ligands include weak bases such as amines, phosphines, ethers, carboxylates, dienes, hydrocarbyl radicals having from 1 to 20 carbon atoms, hydrides or halogens and the like or a combination thereof In another embodiment, two or more Q's form a part of a fused ring or ring system. Other examples of Q ligands include those substituents for R as described above and including cyclobutyl, cyclohexyl, heptyl, tolyl, trifluromethyl, tetramethylene, pentamethylene, methylidene, methyoxy, ethyoxy, propoxy, phenoxy, bis(N-methylanilide), dimethylamide, dimethylphosphide radicals and the like.

In another embodiment, the activator composition of the invention is utilized with the bulky ligand metallocene catalyst compounds of formula (VI) where $L^A$ and $L^B$ are bridged to each other by at least one bridging group, A, as represented in the following formula:

$$L^A A L^B M Q_n \qquad (VI)$$

These bridged compounds represented by formula (VI) are known as bridged, bulky ligand metallocene catalyst compounds. $L^A$, $L^B$, M, Q and n are as defined above. Non-limiting examples of bridging group A include bridging groups containing at least one Group 13 to 16 atom, often referred to as a divalent moiety such as but not limited to at least one of a carbon, oxygen, nitrogen, silicon, aluminum, boron, germanium and tin atom or a combination thereof. Preferably bridging group A contains a carbon, silicon or germanium atom, most preferably A contains at least one silicon atom or at least one carbon atom. The bridging group A may also contain substituent groups R as defined above including halogens and iron. Non-limiting examples of bridging group A may be represented by R'$_2$C, R'$_2$Si, R'$_2$SiR'$_2$Si, R'$_2$Ge, R'P, where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system. In one embodiment, the bridged, bulky ligand metallocene catalyst compounds of formula (VI) have two or more bridging groups A (EP 664 301 B1).

In another embodiment, the activator composition of the invention may be utilized with bulky ligand metallocene catalyst compounds where the R substituents on the bulky ligands $L^A$ and $L^B$ of formulas (V) and (VI) are substituted with the same or different number of substituents on each of the bulky ligands. In another embodiment, the bulky ligands $L^A$ and $L^B$ of formulas (V) and (VI) are different from each other.

In another embodiment, the activator composition of the invention may be utilized with other bulky ligand metallocene catalyst compounds such as those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517 and 5,939,503 and PCT publications WO 93/08221, WO 93/08199, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-B1-0 632 819, EP-B1-0 748 821 and EP-B1-0 757 996, all of which are fully incorporated herein by reference.

In another embodiment, the activator composition of the invention may be utilized with bulky ligand metallocene catalysts which include bridged heteroatom, mono-bulky ligand metallocene compounds. These types of catalysts and catalyst systems are described in, for example, PCT publication WO 92/00333, WO 94/07928, WO 91/04257, WO 94/03506, W096/00244, WO 97/15602 and WO 99/20637 and U.S. Pat. Nos. 5,057,475, 5,096,867, 5,055,438, 5,198, 401, 5,227,440 and 5,264,405 and European publication EP-A-0 420 436, all of which are herein fully incorporated by reference.

In this embodiment, the activator compositions of the invention are utilized with a bulky ligand metallocene catalyst compound represented by formula (VII):

$$L^C AJMQ_n \qquad (VII)$$

where M is a Group 3 to 16 metal atom or a metal selected from the Group of actinides and lanthanides of the Periodic Table of Elements, preferably M is a Group 4 to 12 transition metal, and more preferably M is a Group 4, 5 or 6 transition metal, and most preferably M is a Group 4 transition metal in any oxidation state, especially titanium; $L^C$ is a substituted or unsubstituted bulky ligand bonded to M; J is bonded to M; A is bonded to M and J; J is a heteroatom ancillary ligand; and A is a bridging group; Q is a univalent anionic ligand; and n is the integer 0,1 or 2. In formula (VII) above, $L^C$, A and J form a fused ring system. In an embodiment, $L^C$ of formula (VII) is as defined above for $L^A$, A, M and Q of formula (VII) are as defined above in formula (V).

In formula (VII) J is a heteroatom containing ligand in which J is an element with a coordination number of three from Group 15 or an element with a coordination number of two from Group 16 of the Periodic Table of Elements. Preferably J contains a nitrogen, phosphorus, oxygen or sulfur atom with nitrogen being most preferred.

In another embodiment, the activator composition of the invention is utilized with a bulky ligand type metallocene catalyst compound which is a complex of a metal, preferably a transition metal, a bulky ligand, preferably a substituted or unsubstituted pi-bonded ligand, and one or more heteroallyl moieties, such as those described in U.S. Pat. Nos. 5,527,752 and 5,747,406 and EP-B1-0 735 057, all of which are herein fully incorporated by reference.

In another embodiment the activator composition of the invention is utilized with a ligand metallocene catalyst compound which may be represented by formula VIII:

$$L^D MQ_2(YZ)X_n \qquad (VIII)$$

where M is a Group 3 to 16 metal, preferably a Group 4 to 12 transition metal, and most preferably a Group 4, 5 or 6 transition metal; $L^D$ is a bulky ligand that is bonded to M; each Q is independently bonded to M and $Q_2$(YZ) forms a unicharged polydentate ligand; A or Q is a univalent anionic ligand also bonded to M; X is a univalent anionic group when n is 2 or X is a divalent anionic group when n is 1; n is 1 or 2.

In formula (VIII), L and M are as defined above for formula (V). Q is as defined above for formula (V), preferably Q is selected from the group consisting of —O—, —NR—, —CR$_2$— and —S—; Y is either C or S; Z is selected from the group consisting of —OR, —NR$_2$, —CR$_3$, —SR, —SiR$_3$, —PR$_2$, —H, and substituted or unsubstituted aryl groups, with the proviso that when Q is —NR— then Z is selected from one of the group consisting of —OR, —NR$_2$, —SR, —SiR$_3$, —PR$_2$ and —H; R is selected from a group containing carbon, silicon, nitrogen, oxygen, and/or phosphorus, preferably where R is a hydrocarbon group containing from 1 to 20 carbon atoms, most preferably an alkyl, cycloalkyl, or an aryl group; n is an integer from 1 to 4, preferably 1 or 2; X is a univalent anionic group when n is 2 or X is a divalent anionic group when n is 1; preferably X is a carbamate, carboxylate, or other heteroallyl moiety described by the Q, Y and Z combination.

In another embodiment, the activator composition of the invention is utilized with a the bulky ligand metallocene catalyst compounds, which include heterocyclic ligand complexes where the bulky ligands, the ring(s) or ring system(s), include one or more heteroatoms or a combination thereof. Non-limiting examples of heteroatoms include a Group 13 to 16 element, preferably nitrogen, boron, sulfur, oxygen, aluminum, silicon, phosphorous and tin. Examples of these bulky ligand metallocene catalyst compounds are described in WO 96/33202, WO 96/34021, WO 97/17379 and WO 98/22486 and EP-A1-0 874 005 and U.S. Pat. Nos. 5,637, 660, 5,539,124, 5,554,775, 5,756,611, 5,233,049, 5,744,417, and 5,856,258 all of which are herein incorporated by reference.

In another embodiment, the activator composition of the invention may be utilized with bulky ligand metallocene catalyst compounds, which include complexes known as transition metal catalysts based on bidentate ligands containing pyridine or quinoline moieties, such as those described in U.S. application Ser. No. 09/103,620 filed Jun. 23, 1998, which is herein incorporated by reference. In another embodiment, the bulky ligand metallocene catalyst compounds are those described in PCT publications WO 99/01481 and WO 98/42664, which are fully incorporated herein by reference.

In another embodiment, the activator composition of the invention may be utilized with a bulky ligand metallocene catalyst compounds which may be represented by formula IX:

$$((Z)XA_t(YJ))_q MQ_n \qquad (IX)$$

where M is a metal selected from Group 3 to 13 or lanthanide and actinide series of the Periodic Table of Elements; Q is bonded to M and each Q is a monovalent, bivalent, or trivalent anion; X and Y are bonded to M; one or more of X and Y are heteroatoms, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms, preferably Z is a cyclic group containing 3 to 50 atoms, preferably 3 to 30 carbon atoms; t is 0 or 1; when t is 1, A is a bridging group joined to at least one of X,Y or J, preferably X and J; q is 1 or 2; n is an integer from 1 to 4 depending on the oxidation state of M. In one embodiment, where X is oxygen or sulfur then Z is optional. In another embodiment, where X is nitrogen or phosphorous then Z is present. In an embodiment, Z is preferably an aryl group, more preferably a substituted aryl group.

It is also within the scope of this invention, in one embodiment, that the bulky ligand metallocene catalyst compounds, which may be utilized with the activator composition of the invention include complexes of $Ni^{2+}$ and $Pd^{2+}$ described in the articles Johnson, et al., "New Pd(II)- and Ni(II)-Based Catalysts for Polymerization of Ethylene and a-Olefins", J. Am. Chem. Soc. 1995, 117, 6414–6415 and Johnson, et al., "Copolymerization of Ethylene and Propylene with Functionalized Vinyl Monomers by Palladium(II) Catalysts", J. Am. Chem. Soc., 1996, 118, 267–268, and WO 96/23010 published Aug. 1, 1996, WO 99/02472, U.S. Pat. Nos. 5,852,145, 5,866,663 and 5,880,241, which are all herein fully incorporated by reference. These complexes can be either dialkyl ether adducts, or alkylated reaction products of the described dihalide complexes that can be activated to a cationic state by the activators of this invention described below.

Also included as bulky ligand metallocene catalyst are those diimine based ligands of Group 8 to 10 metal compounds disclosed in PCT publications WO 96/23010 and WO 97/48735 and Gibson, et. al., Chem. Comm., pp. 849–850 (1998), all of which are herein incorporated by reference.

Other bulky ligand metallocene catalysts, which may be utilized with the activator composition of the invention, are those Group 5 and 6 metal imido complexes described in EP-A2-0 816 384 and U.S. Pat. No. 5,851,945, which is incorporated herein by reference. In addition, bridged bis (amido) catalyst compounds are described in WO 96/27439, which is herein incorporated by reference. Other bulky ligand metallocene catalysts are described as bis(hydroxy aromatic nitrogen ligands) in U.S. Pat. No. 5,852,146, which is incorporated herein by reference. Other metallocene catalysts containing one or more Group 15 atoms include those described in WO 98/46651, which is herein incorporated herein by reference. Still another metallocene bulky ligand metallocene catalysts include those multinuclear bulky ligand metallocene catalysts as described in WO 99/20665, which is incorporated herein by reference.

It is also contemplated that in one embodiment, the bulky ligand metallocene catalysts of the invention described above include their structural or optical or enantiomeric isomers (meso and racemic isomers, for example see U.S. Pat. No. 5,852,143, incorporated herein by reference) and mixtures thereof.

Group 15 Containing Polymerization Catalyst

The activator compositions of the invention may also be utilized with metal containing Group 15 polymerization catalyst compounds. Generally, these catalysts includes a Group 3 to 14 metal atom, preferably a Group 3 to 7, more preferably a Group 4 to 6, and even more preferably a Group 4 metal atom, bound to at least one leaving group and also bound to at least two Group 15 atoms, at least one of which is also bound to a Group 15 or 16 atom through another group.

Preferably, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and may optionally be bound to hydrogen, a halogen, a heteroatom or a hydrocarbyl group, or a heteroatom containing group.

In another embodiment of the invention the composition containing alternating atoms of Group 14 and Group 16 may be used to create solutions or emulsions including one or more bulky ligand metallocene-type catalyst compounds, and one or more conventional-type catalyst compounds or catalyst systems. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031 and PCT Publication WO 96/23010 published August 1, 1996, all of which are herein fully incorporated by reference.

Metal containing Group 15 catalyst compounds may be represented by the formulae:

Formula X or

Formula XI wherein

M is a Group 3 to 12 transition metal or a Group 13 or 14 main group metal, preferably a Group 4, 5, or 6 metal, and more preferably a Group 4 metal, and most preferably zirconium, titanium or hafnium, each X is independently a leaving group, preferably, an anionic leaving group, and more preferably hydrogen, a hydrocarbyl group, a heteroatom or a halogen, and most preferably an alkyl y is 0 or 1 (when y is 0 group L' is absent), n is the oxidation state of M, preferably +3, +4, or +5, and more preferably +4, m is the formal charge of the YZL or the YZL' ligand, preferably 0, −1, −2 or −3, and more preferably −2, L is a Group 15 or 16 element, preferably nitrogen, L' is a Group 15 or 16 element or Group 14 containing group, preferably carbon, silicon or germanium, Y is a Group 15 element, preferably nitrogen or phosphorus, and more preferably nitrogen, Z is a Group 15 element, preferably nitrogen or phosphorus, and more preferably nitrogen, $R^1$ and $R^2$ are independently a $C_1$ to $C_{20}$ hydrocarbon group, a heteroatom containing group having up to twenty carbon atoms, silicon, germanium, tin, lead, or phosphorus, preferably a $C_2$ to $C_{20}$ alkyl, aryl or aralkyl group, more preferably a linear, branched or cyclic $C_2$ to $C_{20}$ alkyl group, most preferably a $C_2$ to $C_6$ hydrocarbon group.

$R^3$ is absent or a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen $R^4$ and $R^5$ are independently an alkyl group, an aryl group, substituted aryl group, a cyclic alkyl group, a substituted cyclic alkyl group, a cyclic aralkyl group, a substituted cyclic aralkyl group or multiple ring system, preferably having up to 20 carbon atoms, more preferably between 3 and 10 carbon atoms, and even more preferably a $C_1$ to $C_{20}$ hydrocarbon group, a $C_1$ to $C_{20}$ aryl group or a $C_1$ to $C_{20}$ aralkyl group, or a heteroatom containing group, for example $PR_3$, where R is an alkyl group, $R^1$ and $R^2$ may be interconnected to each other, and/or $R^4$ and $R^5$ may be interconnected to each other, $R^6$ and $R^7$ are independently absent, or hydrogen, an alkyl group, halogen, heteroatom or a hydrocarbyl group, preferably a linear, cyclic or branched alkyl group having 1 to 20 carbon atoms, more preferably absent, and $R^*$ is absent, or is hydrogen, a Group 14 atom containing group, a halogen, a heteroatom containing group.

By "formal charge of the YZL or YZL' ligand", it is meant the charge of the entire ligand absent the metal and the leaving groups X.

By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

Phenoxide Transition Metal Catalyst Compositions

The activator compositions of the invention may also be used with phenoxide transtion metal catalyst compounds. Generally, these complexes are heteroatom substituted phenoxide ligated Group 3 to 10 transition metal or lanthanide metal compounds wherein the metal is bound to the oxygen of the phenoxide group.

Phenoxide transition metal catalyst compounds may be represented by formula XII or XIII below:

XII or

XIII wherein $R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not also be bound to M;

at least one of $R^2$ to $R^5$ is a heteroatom containing group, the rest of $R^2$ to $R^5$ are independently hydrogen or a $C_1$ to $C_{100}$ group, preferably a $C_4$ to $C_{20}$ alkyl group, preferred examples of which include butyl, isobutyl, t-butyl, pentyl, hexyl, heptyl, isohexyl, octyl, isooctyl, decyl, nonyl, dodecyl, and any of $R^2$ to $R^5$ also may or may not be bound to M;

Each $R^1$ to $R^5$ group may be independently substituted or unsubstituted with other atoms, including heteroatoms or heteroatom containing group(s);

O is oxygen;

M is a Group 3 to Group 10 transition metal or lanthanide metal, preferably a Group 4 metal, preferably M is Ti, Zr or Hf;

n is the valence state of the metal M, preferably 2, 3, 4, or 5; and

Q is, and each Q may be independently be, an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon, silicon or another heteroatom. Preferred heteroatoms include boron, aluminum, silicon, nitrogen, phosphorus, arsenic, tin, lead, antimony, oxygen, selenium, tellurium. Particularly preferred heteroatoms include nitrogen, oxygen, phosphorus, and sulfur. Even more particularly preferred heteroatoms include nitrogen and oxygen. The heteroatom itself may be directly bound to the phenoxide ring or it may be bound to another atom or atoms that are bound to the phenoxide ring. The heteroatom containing group may contain one or more of the same or different heteroatoms. Preferred heteroatom containing groups include imines, amines, oxides, phosphines, ethers, ketones, oxoazolines heterocyclics, oxazolines, thioethers, and the like. Particularly preferred heteroatom containing groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment the heteroatom substituted phenoxide transition metal compound is an iminophenoxide Group 4 transition metal compound, and more preferably an iminophenoxidezirconium compound.

In another embodiment, it is further contemplated that the above catalysts or catalyst systems may be used in combination with the activator(s) of the present invention.

Supports, Carriers and General Supporting Techniques

The activator complexes of the invention and/or the polymerization catalyst compound may be combined with one or more support materials or carriers, using one of the support methods known in the art or as described below. For example, in a one embodiment the activator composition is in a supported form, for example deposited on, contacted with, vaporized with, bonded to, or incorporated within, adsorbed or absorbed in, or on, a support or carrier. In another embodiment, the activator and a catalyst compound may be deposited on, contacted with, vaporized with, bonded to, or incorporated within, adsorbed or absorbed in, or on, a support or carrier.

The terms "support" or "carrier", for purposes of this patent specification, are used interchangeably and are any support material, preferably a porous support material, including inorganic or organic support materials. Non-limiting examples of inorganic support materials include inorganic oxides and inorganic chlorides. Other carriers include resinous support materials such as polystyrene, functionalized or crosslinked organic supports, such as polystyrene, divinyl benzene, polyolefins, or polymeric compounds, zeolites, talc, clays, or any other organic or inorganic support material and the like, or mixtures thereof The preferred carriers are inorganic oxides that include those Group 2, 3, 4, 5, 13 or 14 metal oxides. The preferred supports include silica, alumina, silica-alumina, magnesium chloride, and mixtures thereof. Other useful supports include magnesia, titania, zirconia, montmorillonite (EP-B1 0 511 665), phyllosilicate, and the like. Also, combinations of these support materials may be used, for example, silica-chromium, silica-alumina, silica-titania and the like. Additional support materials may include those porous acrylic polymers described in EP 0 767 184 B1, which is incorporated herein by reference.

It is preferred that the carrier, most preferably an inorganic oxide, has a surface area in the range of from about 10 to about 700 $m^2/g$, pore volume in the range of from about 0.1 to about 4.0 cc/g and average particle size in the range of from about 5 to about 500 $\mu$m. More preferably, the surface area of the carrier is in the range of from about 50 to about 500 $m^2/g$, pore volume of from about 0.5 to about 3.5 cc/g and average particle size of from about 10 to about 200 $\mu$m. Most preferably the surface area of the carrier is in the range from about 100 to about 400 $m^2/g$, pore volume from about 0.8 to about 3.0 cc/g and average particle size is from about 5 to about 100 $\mu$m. The average pore size of the carrier of the invention typically has pore size in the range of from 10 to 1000 Å, preferably 50 to about 500 Å, and most preferably 75 to about 350 Å.

Examples of supporting bulky ligand metallocene-type catalyst systems, which may be used to support the activator and/or catalyst systems of the invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032, 5,770,664, 5,846,895 and 5,939,348 and U.S. application Ser. No. 271,598 filed Jul. 7, 1994 and Ser. No. 788,736 filed Jan. 23, 1997 and PCT publications WO 95/32995, WO 95/14044, WO 96/06187 and WO 97/02297, and EP-B1-0 685 494 all of which are herein fully incorporated by reference.

There are various other methods in the art for supporting the polymerization catalyst systems of the invention. For example, the bulky ligand metallocene-type catalyst compound of the invention may contain a polymer bound ligand as described in U.S. Pat. Nos. 5,473,202 and 5,770,755, which is herein fully incorporated by reference; the bulky ligand metallocene-type catalyst system of the invention may be spray dried as described in U.S. Pat. No. 5,648,310, which is herein fully incorporated by reference; the support used with the bulky ligand metallocene-type catalyst system of the invention may be functionalized as described in European publication EP-A-0 802 203, which is herein fully incorporated by reference, or at least one substituent or leaving group may be selected as described in U.S. Pat. No. 5,688,880, which is herein fully incorporated by reference.

In another embodiment, an antistatic agent or surface modifier, that is used in the preparation of the supported catalyst system as described in PCT publication WO 96/11960, which is herein fully incorporated by reference, may be used with catalyst systems including the activator compounds of the invention,. The catalyst systems of the invention may also be prepared in the presence of an olefin, for example hexene-1.

In another embodiment, activator and/or catalyst system of the invention may be combined with a carboxylic acid salt of a metal ester, for example aluminum carboxylates such as aluminum mono, di- and tri- stearates, aluminum octoates, oleates and cyclohexylbutyrates, as described in U.S. application Ser. No. 09/113,216, filed Jul. 10, 1998.

In another embodiment there is a method for producing a supported bulky ligand metallocene-type catalyst system, which maybe used to support the activator of the invention which is described below, and is described in U.S. application Ser. No. 265,533, filed Jun. 24, 1994 and Ser. No. 265,532, filed Jun. 24, 1994 and PCT publications WO 96/00245 and WO 96/00243 both published Jan. 4, 1996, all of which are herein fully incorporated by reference. In this method, the catalyst compound is slurried in a liquid to form a catalyst solution or emulsion. A separate solution is formed containing the activator. The liquid may be any compatible solvent or other liquid capable of forming a solution or the like with the catalyst compounds and/or activator. In the most preferred embodiment the liquid is a cyclic aliphatic or aromatic hydrocarbon, most preferably toluene. The catalyst compound and activator solutions are mixed together heated and added to a heated porous support or a heated porous support is added to the solutions such that the total volume of the bulky ligand metallocene-type catalyst compound solution and the activator solution or the bulky ligand metallocene-type catalyst compound and activator solution is less than four times the pore volume of the porous support, more preferably less than three times, even more preferably less than two times; preferred ranges being from 1.1 times to 3.5 times range and most preferably in the 1.2 to 3 times range.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration,* Vol. 28, No. 3, Analytical Chemistry 332–334 (March, 1956).

Polymerization Process

The activators of the invention, catalyst systems and supported catalyst systems utilizing the activators described above are suitable for use in any prepolymerization and/or polymerization process over a wide range of temperatures and pressures. The temperatures may be in the range of from −60° C. to about 280° C., preferably from 50° C. to about 200° C., and the pressures employed may be in the range from 1 atmosphere to about 500 atmospheres or higher.

Polymerization processes include solution, gas phase, slurry phase and a high pressure process or a combination thereof. Particularly preferred is a gas phase or slurry phase polymerization of one or more olefins at least one of which is ethylene or propylene.

In one embodiment, the process of the invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1, 4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In another embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421 all of which are herein fully incorporated by reference.

In another embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In another embodiment, the polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555 and PCT WO 99/32525, which are fully incorporated herein by reference.

In one embodiment of the process of the invention is the process, preferably a slurry or gas phase process is operated in the presence of the catalyst system of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. Nos. 5,712,352 and 5,763,543, which are herein fully incorporated by reference.

In another embodiment, the method of the invention provides for injecting a the catalyst system of the invention into a reactor, particularly a gas phase reactor. In one embodiment the catalyst system is used in the unsupported form, preferably in a liquid form such as described in U.S. Pat. Nos. 5,317,036 and 5,693,727 and European publication EP-A-0 593 083, all of which are herein incorporated by reference. The polymerization catalyst in liquid form can be fed with an activator, and/or a support, and/or a supported activator together or separately to a reactor. The injection methods described in PCT publication WO 97/46599, which is fully incorporated herein by reference, may be utilized. Where an unsupported catalyst system is used the mole ratio of the metal of the Lewis acid activator component to the metal of the phenoxide transition metal catalyst compound is in the range of between 0.3:1 to 10,000:1, preferably 100:1 to 5000:1, and most preferably 500:1 to 2000:1.

Polymer Products

The polymers produced by the process of the invention can be used in a wide variety of products and end-use applications. The polymers produced by the process of the invention include linear low density polyethylene, elastomers, plastomers, high density polyethylenes, medium density polyethylenes, low density polyethylenes, polypropylene and polypropylene copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced by the process of the invention typically have a molecular weight distribution, a weight average molecular weight to number average molecular weight ($M_w/M_n$) of greater than 1.5 to about 15, particularly greater than 2 to about 10, more preferably greater than about 2.2 to less than about 8, and most preferably from 2.5 to 8.

Also, the polymers of the invention typically have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993, which is fully incorporated herein by reference.

The polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%.

In another embodiment, polymers produced using a catalyst system of the invention have a CDBI less than 50%, more preferably less than 40%, and most preferably less than 30%.

The polymers of the present invention in one embodiment have a melt index (MI) or ($I_2$) as measured by ASTM-D-1238-E in the range from no measurable flow to 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$) ($I_{21}$ is measured by ASTM-D-1238-F) of from 10 to less than 25, more preferably from about 15 to less than 25.

The polymers of the invention in a preferred embodiment have a melt index ratio ($I_{21}/I_2$) ($I_{21}$ is measured by ASTM-D-1238-F) of from preferably greater than 25, more preferably greater than 30, even more preferably greater that 40, still even more preferably greater than 50 and most preferably greater than 65. In an embodiment, the polymer of the invention may have a narrow molecular weight distribution and a broad composition distribution or vice-versa, and may be those polymers described in U.S. Pat. No. 5,798,427 incorporated herein by reference.

In yet another embodiment, propylene based polymers are produced in the process of the invention. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117, all of which are herein incorporated by reference.

The polymers of the invention may be blended and/or coextruded with any other polymer. Non-limiting examples of other polymers include linear low density polyethylenes, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

EXAMPLES

In order to provide a better understanding of the present invention including representative advantages thereof, the following examples are offered.

Tris-pentafluorophenylaluminum $Al(C_6F_5)_3$ was synthesized via the reaction of one equivalent of tris-pentafluorophenylborane $B(C_6F_5)_3$ (from Boulder Scientific, Mead, Colo.) with one equivalent of trimethylaluminum as described by Paolo Biagini et al. in U.S. Pat. No. 5,602,269. $[CH_3Al(C_6F_5)_2]_2$ was synthesized by dissolving $B(C_6F_5)_3$ in toluene previously dried over sodium/potassium alloy and adding dropwise two equivalents of trimethylaluminum. The solvent was removed under vacuum, pentane was added, and the solution cooled to −30° C. Anhydrous toluene and pentane were purchased from Aldrich, Milwaukee, Wis. Triphenylmethanol $(C_6H_5)_3COH$ was also purchased from Aldrich and used as received. X-Ray Diffraction studies were performed by Crystalytics Company.

Example 1

Figure 1:
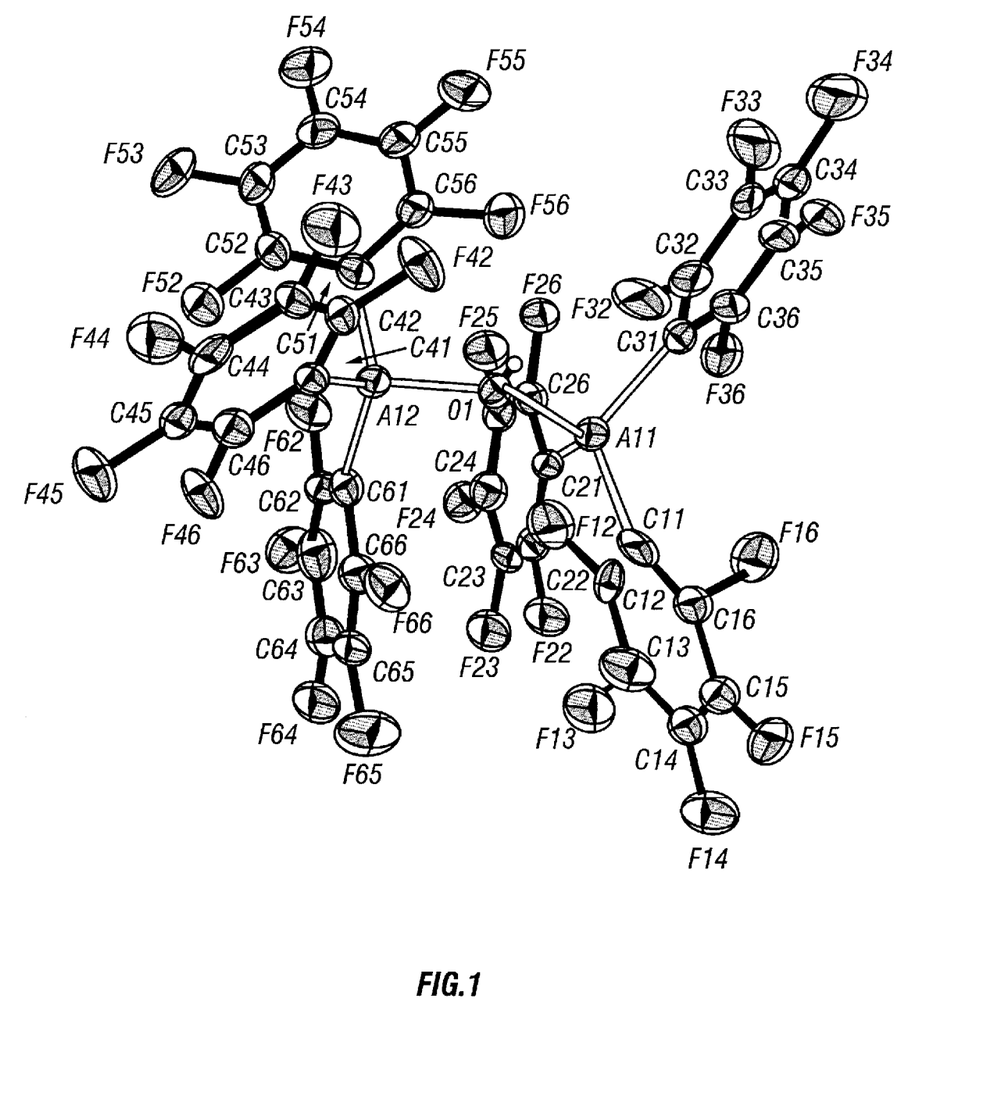
FIG. 1 is an illustration of the complex having the formula: $(C_6H_5)_3C^+[HO(Al(C_6F_5)_3)_2]^-$ prepared in Example 1.
Figure 2:
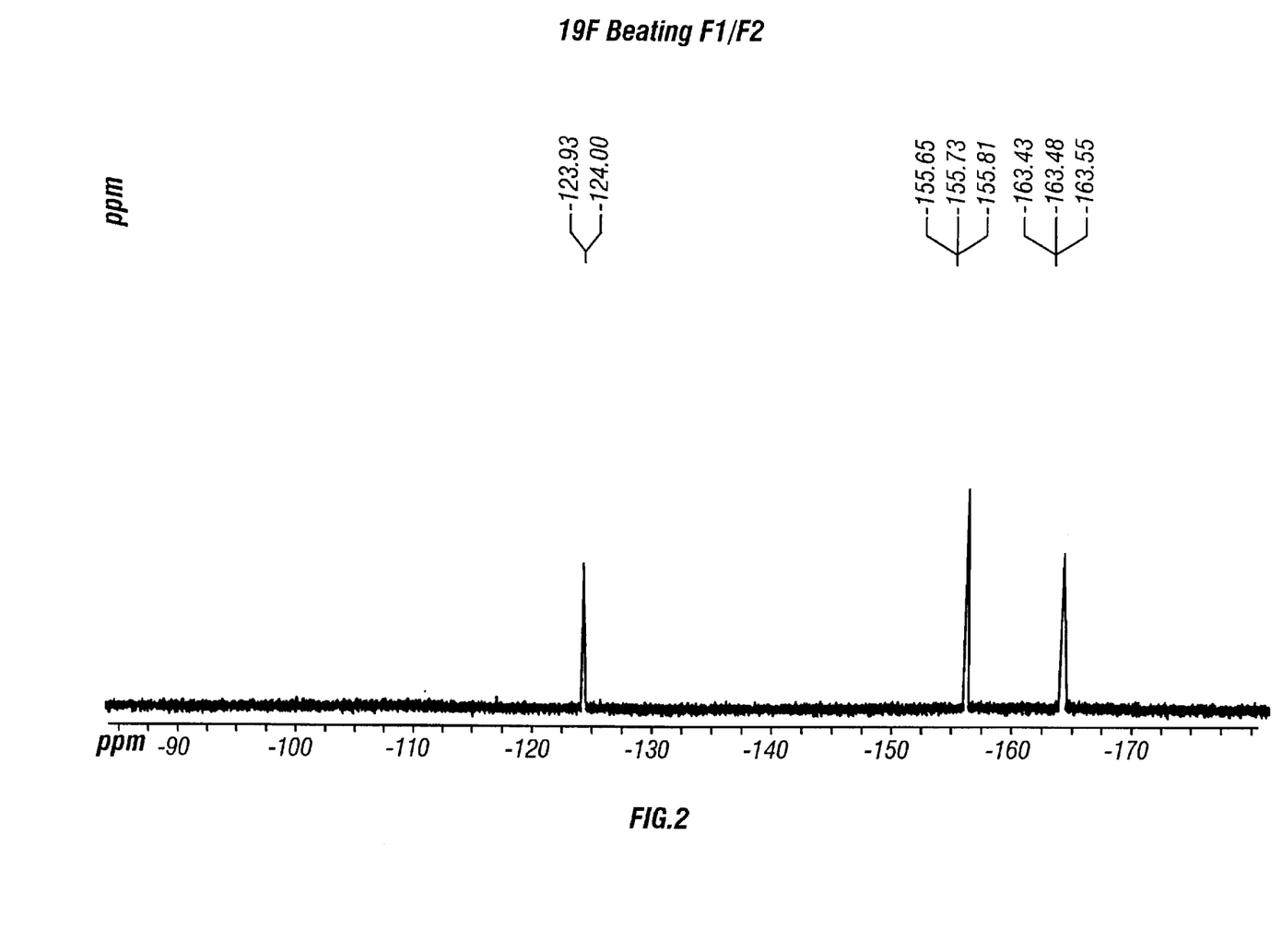
FIG. 2 is an $^{19}F$ NMR of $(C_6H_5)_3C^+[HO(Al(C_6F_5)_3)_2]^-$ prepared in Example 1.

$(C_6H_5)_3C^+[HO(Al(C_6F_5)_3)_2]^-$ Synthesis $Al(C_6F_5)_3$ (5.15 grams) and 2.33 grams of $(C_6H_5)_3COH$ were combined in toluene at room temperature. A dark brick red slurry formed immediately upon mixing the two reagents. A red oil separated from the mixture. The toluene was decanted from the oil and several 30 ml portions of pentane was added to the red oil until the oil crystallized into a yellow solid. Crystals of the complex were grown out of dichloromethane. An X-ray diffraction study of a crystal of this complex revealed a dimer complex in the solid state with the following formula: $(C_6H_5)_3C^+[HO(Al(C_6F_5)_3)_2]^-$. (FIG. 1). $^{19}F$ NMR $(CD_2Cl_2)$; ref. to $CF_3C_6H_5$ $\delta$=−62.5: $\delta$ (d, −121.93), (t, −155.65),(m, −163.49). $^1H$ NMR $(CD_2Cl_2)$; $\delta$(s, 5.18), (d, 7.67), (t, 7.89), (t, 8.29). (FIG. 2).

Example 2
[Me$_2$AlOC(C$_6$H$_5$)$_3$]$_2$ Synthesis 10.0 grams of trimethylaluminum was combined with one equivalent of (C$_6$H$_5$)$_3$COH in toluene. A white precipitate forms which was filtered, washed with pentane and dried under vacuum. $^1$H NMR (C$_6$D$_6$); d (s, -0.735), (m, 7.18), (d, 7.67).

Example 3
(C$_6$H$_5$)$_3$C$^+$[Me$_x$(C$_6$F$_5$)$_y$OAln]$^-$ Synthesis

Al(C$_6$F$_5$)$_3$(toluene) (9.08 grams) and 5.0 grams of [Me$_2$AlOC(C$_6$H$_5$)$_3$]$_2$ were combined in benzene at room temperature. A dark brick red slurry formed immediately upon mixing the two reagents. A red oil separated from the mixture. The toluene was decanted from the oil and several 30 ml portions of pentane was added to the red oil until the oil crystallized into a orange solid. (C$_6$H$_5$)$_3$CCH$_3$ (1.75 grams) was isolated from the pentane fractions. $^1$H NMR (CD$_2$Cl$_2$); $\delta$(0--1.5 broad lump —Al—CH$_3$), (d, 7.66), (t, 7.89), (t, 8.29). $^{19}$F NMR (C$_6$D$_6$; $\delta$(-120--125 broad with spikes (doublets)), (-149--159 broad with spikes (triplets)), (-160--166 broad with spikes (multiplets)). Elemental Analysis; Carbon, 47.63%; Hydrogen, 1.46%; Fluorine, 36.32%.

The polymerization reactions of Examples 4 to 7 were conducted in a stainless steel, 1-liter Zipperclave autoclave reactor. The reactor was equipped with water jacket for heating and cooling. Injections were typically done through a septum inlet or were injected via a high pressure nitrogen injection. Before polymerization the reactor was purged with nitrogen for several hours at 100° C. Upon injection of catalyst, ethylene was fed continuously on demand keeping the reactor pressure constant while maintaining the reaction temperature at 60° C. The reaction was stopped by cooling and venting the pressure and exposing the contents of the reactor to air. The liquid components were evaporated and the poly(ethylene-co-hexene-1) was dried in a vacuum oven. Weight average molecular weight (M$_w$), number average molecular weight (M$_n$) and their ratio M$_w$/M$_n$ were obtained by GPC gel permeation chromatography.

Example 4

(n-BuCP)$_2$Zr(CH$_3$)$_2$) (20 mg) and (C$_6$H$_5$)$_3$C$^+$[HO(Al(C$_6$F$_5$)$_3$)$_2$]$^-$ (79 mg) were combined in 10 mls of toluene. 2 mls of the catalyst precursor solution was injected into a 1L stainless steel reactor preheated to 60° C. containing 45 mls of hexene, 75 psi (517 kPa) of ethylene, and 400 mls of toluene. After 15 minutes the polymerization reaction was stopped. Polymer was not obtained.

Example 5

(n-BuCP)$_2$Zr(CH$_3$)$_2$) (20 mg) and (C$_6$H$_5$)$_3$C$^+$[HO(Al(C$_6$F$_5$)$_3$)$_2$]$^-$/(5☐1 Me$_3$Al) (79 mg) were combined in 10 mls of toluene. 2 mls of the catalyst precursor solution (light blue) was injected into a 1 L stainless steel reactor preheated to 60° C. containing 45 mls of hexene, 75 psi (517 kPa) of ethylene, and 400 mls of toluene. After 15 minutes the polymerization reaction was stopped and 6.10 grams of polymer were isolated. Mw=260,000, Mn=135000, Mw/Mn=1.92; Hexene wt %=2.4.

Example 6

(n-BuCP)$_2$Zr(CH$_3$)$_2$) (20 mg) and (C$_6$H$_5$)$_3$C$^+$[Me$_x$(C$_6$F$_5$)$_y$OAl]$^-$ (79 mg) were combined in 10 mls of toluene. 2 mls of the catalyst precursor solution was injected into a 1L stainless steel reactor preheated to 60° C. containing 45 mls of hexene, 75 psi (517 kPa) of ethylene, and 400 mls of toluene. After 30 minutes the polymerization reaction was stopped and 27.5 grams of polymer were isolated. Mw=592000, Mn=288000, Mw/Mn=2.05; Hexene wt %.

Example 7
Ethylene-Hexene Copolymerizations

{[(2,4,6-Me$_3$C$_6$H$_2$)NCH$_2$CH$_2$]$_2$NH}Hf(CH$_2$Ph)$_2$ (22 mg) and (C$_6$H$_5$)$_3$C$^+$[Me$_x$(C$_6$F$_5$)$_y$O$_n$Al$_m$]$^-$ (46 mg) were combined in 10 mls of toluene. 2 mls of the catalyst solution was injected into a 1 L stainless steel reactor preheated to 60° C. containing 45 mls of hexene, 75 psi (517 kPa) of ethylene, and 400 mls of toluene. After 30 minutes the polymerization reaction was stopped and 11.0 grams of polymer were isolated. Run 2: 2×2 mls of catalyst solution were injected into the reactor and 26.8 grams of polymer were isolated. Mw=116,000, Mn=63,900, Mw/Mn=1.81; Hexene wt %=38.5. Run 2: 2×2 mls of catalyst solution were injected into the reactor and 26.8 grams of polymer were isolated. Mw=208,000, Mn=62,600, Mw/Mn=1.96; Hexene wt %=37.1.

Example 8
Catalyst A Synthesis 4.0 grams of silica (Davison 948, calcined at 600° C.) was slurried in toluene. 0.758 grams of Me$_2$AlOC(C$_6$H$_5$)$_3$ and 0.92 grams of Al(C$_6$F$_5$)$_3$(toluene) were added to the silica slurry. The resulting dark red slurry was stirred for one hour and left to sit overnight. The following day the slurry was filtered, washed with toluene and dried under vacuum forming a free flowing orange solid. (5.1 grams). 2.5 grams of this supported activator was combined in toluene with 0.1 grams of (n-BuCP)$_2$Zr(CH$_3$)$_2$. The slurry was stirred for one hour, filtered, rinsed with toluene, and dried under vaccuum.

Example 9
Catalyst B Synthesis

Tris-pentafluorophenylaluminum was reacted with silica (Davison 948, 600° C.) to liberate pentafluorobenzene in a toluene slurry. After approximately 24 hours the slurry was filtered and washed with three 50 ml portions of toluene. The resulting silica was reacted with 2.34 grams of triphenylmethanol. An immediate dark brick red color forms in the silica. After one hour the silica was rinsed with toluene, and combined with 5.17 grams of Al(C$_6$F$_5$)$_3$(toluene). The slurry was stirred for one hour, filtered, rinsed with toluene (3 50 ml portions) and dried overnight under vacuum. A free-flowing yellow solid resulted. 2.0 grams of this supported activator was combined in toluene with 0.1 grams of (n-BuCP)$_2$Zr(CH$_3$)$_2$. The slurry was stirred for one hour, filtered, rinsed with toluene, and dried under vaccuum.

Example 10
(C$_6$H$_5$)$_3$COC$_6$F$_4$C$_6$F$_5$ Synthesis 2,3,5,6-tetrafluoro-4-pentafluorophenylphenol (15.3 grams) was combined with one equivalent of potassium hydride (1.8 grams) in a tetrahydrofuran solution. The evolution of hydrogen gas resulted, yielding a colorless solution. Triphenylmethyl chloride (12.8 grams) was added to the solution. A white precipitate formed after stirring several hours, the tetrahydrofuran was removed and replaced with dichloromethane. The slurry was filtered, and the potassium chloride salt was washed with several mls of dichloromethane. The solution was dried under vacuum yielding a white solid (25 grams). $^{19}$F NMR (C$_6$D$_6$); ref. to CF$_3$C$_6$H$_5$ $\delta$=-62.5: $\delta$(m, -134.8), (m, -137.5), (t, -142.2), (t, -146.9), (t, -157.0).

Example 11
Catalyst C Synthesis (C$_6$H$_5$)$_3$COC$_6$F$_4$C$_6$F$_5$ (1.7 grams) was slurried in anhydrous decane with 2.0 grams of triethylaluminum treated silica (1.2 mmoles of triethylaluminum combined in a pentane slurry of Davison 948(calcined at 600° C.), filtered and dried). The slurry was heated overnight at 100° C. The resulting slurry was washed with several 30 ml portions of toluene. (The filtrate contained 0.5 grams of triphenylmethane.) The silica was then tranferred to a 100 ml flask slurried in toluene combined with 0.048 grams of (1,3MeBuCp)$_2$Zr(CH$_3$)$_2$ and stirred at room temp. for one hour. The silica was filtered, rinsed with toluene, and dried under vacuum.

The polymerization reactions of Examples 12 to 14 were conducted in a stainless steel, 1-liter Zipperclave autoclave reactor. The reactor was equipped with water jacket for heating and cooling. Injections were performed via a high pressure nitrogen injection. (400 mls isobutane, 30 mls of hexene, and 15 μls triethylaluminum or 100 μls triisobutylaluminum) Before polymerizations the reactor was purged with nitrogen for several hours at 100° C. Upon injection of catalyst ethylene was fed continuously on demand keeping the reactor pressure constant (130 psig (896 kPa) ethylene) while maintaining the reaction temperature at 85° C. After the allotted time the reaction was stopped by cooling and venting the pressure and exposing the contents of the reactor to air. The liquid components were evaporated and the poly(ethylene-co-hexene-1) resin was dried under a N$_2$ purge. Weight average molecular weight (M$_w$), number average molecular weight (M$_n$) and their ratio M$_w$/M$_n$ were obtained by GPC gel permeation chromatagraphy. Hexene wt % incorporation was obtained from $^1$H NMR data.

Example 12
Slurry-Phase Ethylene-Hexene Polymerization Using Catalyst A

The above procedure was performed using 25 mgs of Catalyst A. After 40 minutes the reaction was stopped. Some reactor fouling was observed and 36.8 grams of polymer resin (2450 g pol./g cat. h) was obtained. Mw=112000, Mn=50000, Mw/Mn=2.24; Hexene wt %=5.7.

Example 13
Slurry-Phase Ethylene-Hexene Polymerization Using Catalyst B

The polymerization was run according to the procedure outlined above using catalyst B. No reactor fouling was observed and the polymer resin yield was Run 1: 53.4 grams (3560 g pol./g cat. h). Mw=92800, Mn=43600, Mw/Mn= 2.13; Hexene wt %=6.4. Run 2: 71.6 grams (4770 g pol./g cat. h). Mw=88300, Mn=40500, Mw/Mn=2.05; Hexene wt %=2.18.

Example 14
Slurry-Phase Ethylene-Hexene Polymerizations Using Catalyst C

The polymerization was run according to the procedure outlined above using catalyst C, The polymer resin yield was Run 1: 50.5 grams (3060 g pol./g cat. h: Run 2: 59.5 grams (3606 g pol./g cat. h). Mw=165,000, Mn=72,700, Mw/Mn= 2.27; Hexene wt %=5.5. Run 2: 59.5 grams (3606 g pol./g cat.h). Mw=165,000, Mn=76,600, Mw/Mn=2.16; Hexene wt %=5.4.

While the present invention has been described and illustrated by reference to particular embodiments, those of ordinary skill in the art will appreciate that the invention lends itself to variations not necessarily illustrated herein. For example, it is contemplated that the activator compositions of the invention may be used in combination with each other and with known actuator compositions to activate polymerization catalyst compound(s). Furthermore, it is contemplated that any one of the embodiment(s) of this invention may be combined with any other embodiment(s) of the invention. For these reasons, then, reference should be made solely to the appended claims for purposes of determining the true scope of the present invention.

I claim:

1. A method of preparing a polymerization catalyst activator comprising:

combining a perfluorophenyl aluminum compound and a trityl compound, where the perfluorophenyl aluminum compound is represented by the formula:

Al(C$_6$F$_5$)$_m$R$_n$ where m+n=3; each R is independently selected from the group consisting of hydrogen, a hydroxyl group, an alkoxy group and an alkyl group, and where the trityl compound is represented by the formula:

(C$_6$H$_5$)$_3$COL where L is a halogenated C$_6$ aromatic, or higher carbon number polycyclic aromatic hydrocarbon or aromatic ring assembly in which two or more rings or fused ring systems are joined together.

2. The method of claim 1 further comprising combining the polymerization catalyst activator with a support.

3. The method of claim 1 where R is a halogenated C$_6$ aromatic, or higher carbon number polycyclic aromatic hydrocarbon or aromatic ring assembly in which two or more rings or fused ring systems are joined together.

4. The method of claim 1 where R is represented by the formula [M$^{k+}$Q$_n$]$^{d-}$ where k is an integer from 1 to 3; n is an integer from 2 to 6; n−k=d; M is an element selected from Group 13 of the Periodic Table of the Elements, and each Q is independently selected from the group consisting of a hydride, bridged or unbridged dialkylamido, halide, alkoxide, aryloxide, hydrocarbyl, substituted hydrocarbyl, halocarbyl, substituted halocarbyl, halosubstituted-hydrocarbyl radicals having up to 20 carbon atoms, and combinations thereof.

5. A method of preparing a polymerization catalyst activator comprising combining a perfluorophenyl aluminum compound is represented by the formula:

(AlO)x(Al)y(C$_6$F$_5$)z(R)d where x cannot be 0 and z+d is $\leq 1+3(x+y)$; each R is independently selected from the group consisting of hydrogen, a hydroxyl group, an alkoxy group, and an alkyl group and a trityl compound represented by the formula:

(C$_6$H$_5$)$_3$COL where L is a halogenated C$_6$ aromatic, or higher carbon number polycyclic aromatic hydrocarbon or aromatic ring assembly in which two or more rings or fused ring systems are joined together.

6. The method of claim 5 where R is a halogenated C$_6$ aromatic or higher carbon number polycyclic aromatic hydrocarbon or aromatic ring assembly in which two or more rings or fused ring systems are joined together.

7. The method of claim 5 where R is represented by the formula $[M^{k+}Q_n]^{d-}$ where k is an integer from 1 to 3; n is an integer from 2 to 6; n−k=d; M is an element selected from Group 13 of the Periodic Table of the Elements, and each Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals having up to 20 carbon atoms.

8. The method of claim 1 where L is selected from the group consisting of a metal moiety, a metalloid moiety, hydrogen, and an alkyl group.

9. The method of claim 1 where L is represented by the formula $[M^{k+}Q_n]^{d-}$ where k is an integer from 1 to 3; n is an integer from 2 to 6; n−k=d; M is an element selected from Group 13 of the Periodic Table of the Elements, and each Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals having up to 20 carbon atoms.

10. The method of claim 8 where the metal moiety is represented by the formula $AlR_2$, $TiR_3$, $Ti(Benzyl)_3$ or $ZrR_3$ where each R is independently hydrogen, a hydroxyl group, or an alkyl group.

11. The method of claim 1 further comprising contacting the polymerization catalyst activator with a polymerization catalyst selected from the group consisting of a bulky ligand metallocene catalyst compound, a metal containing Group 15 polymerization catalyst compound, a phenoxide transition metal catalyst compound, and combinations thereof.

12. The method of claim 2 where the support is selected from the group consisting of silica, triethylaluminum treated silica, and a combination thereof.

13. A method for preparing a supported polymerization catalyst activator comprising the steps of:
   a) combining a perfluorophenyl aluminum compound and a trityl compound to form a polymerization catalyst activator, where the perfluorophenyl aluminum compound is represented by the formula:

$Al(C_6F_5)_mR_n$ where m+n=3; each R is independently selected from the group consisting of hydrogen, a hydroxyl group, and an alkyl group;

or where the perfluorophenyl aluminum compound is represented by the formula:

$(AlO)x(Al)y(C_6F_5)z(R)d$ where x cannot be 0 and z+d is $\leq 1+3(x+y)$; each R is independently selected from the group consisting of hydrogen, a hydroxyl group, an alkoxy group and an alkyl group;

and where the trityl compound is represented by the formula $(C_6H_5)_3COL$ where L is selected from the group consisting of a metal moiety, a metalloid moiety, hydrogen, a hydroxyl group, an alkyl group and a halogenated $C_6$ aromatic, or higher carbon number polycyclic aromatic hydrocarbon or aromatic ring assembly in which two or more rings or fused ring systems are joined together; and b). combining the polymerization catalyst activator with silica.

14. The method of claim 5 where L is selected from the group consisting of a metal moiety, a metalloid moiety, hydrogen, and an alkyl group.

15. The method of claim 13 where L is a metal moiety represented by the formula $AlR_2$, $TiR_3$, $Ti(Benzyl)_3$ or $ZrR_3$ and where each R is independently hydrogen, a hydroxyl group, or an alkyl group.

16. The method of claim 1 where m=0, n=3, R is a alkyl group and L is a halogenated $C_6$ aromatic, or higher carbon number polycyclic aromatic hydrocarbon or aromatic ring assembly in which two or more rings or fused ring systems are joined together.

17. A method of preparing a polymerization activator compound comprising combining a trialkylaluminum treated silica support material and a trityl compound represented by the formula:

$(C_6H_5)_3COL$ where L is a halogenated $C_6$ aromatic, or higher carbon number polycyclic aromatic hydrocarbon or aromatic ring assembly in which two or more rings or fused ring systems are joined together.

* * * * *